United States Patent [19]

Nickias et al.

[11] Patent Number: 5,536,797
[45] Date of Patent: Jul. 16, 1996

[54] SYNDIOTACTIC PROCHIRAL OLEFIN POLYMERIZATION PROCESS

[75] Inventors: Peter N. Nickias, Midland; Karen K. Borodychuk, Mt. Pleasant; Thomas H. Newman, Midland, all of Mich.

[73] Assignee: The Dow Chemical Company, Midland, Mich.

[21] Appl. No.: 316,748

[22] Filed: Oct. 3, 1994

[51] Int. Cl.⁶ .............................. C08F 4/64; C08F 4/642
[52] U.S. Cl. .................. 526/170; 502/103; 526/160; 526/172; 526/336; 526/346; 526/347.1; 526/348
[58] Field of Search .................. 526/160, 170; 502/103

[56] References Cited

U.S. PATENT DOCUMENTS

| | | | |
|---|---|---|---|
| 5,026,798 | 6/1991 | Canich | 526/127 |
| 5,045,517 | 9/1991 | Campbell, Jr. | 502/103 |
| 5,064,802 | 11/1991 | Stevens et al. | 502/155 |
| 5,066,741 | 11/1991 | Campbell, Jr. | 526/171 |
| 5,153,157 | 10/1992 | Hlatky et al. | 502/117 |
| 5,206,197 | 4/1993 | Campbell, Jr. | 502/103 |
| 5,241,025 | 8/1993 | Hlatky | 526/129 |
| 5,252,677 | 12/1993 | Tomita | 525/333.9 |
| 5,296,433 | 3/1994 | Siedle et al. | 502/117 |
| 5,346,925 | 9/1994 | Sugano | 521/54 |
| 5,374,696 | 12/1994 | Rosen | 526/126 |

FOREIGN PATENT DOCUMENTS

| | | |
|---|---|---|
| 277003 | 8/1988 | European Pat. Off. . |
| 468651 | 1/1991 | European Pat. Off. . |
| 520732 | 12/1992 | European Pat. Off. . |
| WO93/03067 | 2/1993 | WIPO . |
| WO93/23412 | 11/1993 | WIPO . |
| WO94/00500 | 1/1994 | WIPO . |

OTHER PUBLICATIONS

J. Chem. Soc. Chem. Comm., 1993, 383–384.
Lambert, J. B. et al., Organometallics, 1994, 13, 2430–2443.

*Primary Examiner*—Fred Zitomer

[57] ABSTRACT

Octahydrofluorenyltitanium metal complexes or ring substituted octahydrofluorenyltitanium metal complexes wherein the metal is in the +2, +3 or +4 formal oxidation state and activating cocatalysts or activating techniques are used to produce catalysts useful for polymerizing prochiral olefins to form highly syndiotactic polymers.

8 Claims, No Drawings

SYNDIOTACTIC PROCHIRAL OLEFIN POLYMERIZATION PROCESS

BACKGROUND OF THE INVENTION

This invention relates to a process for preparing polymers of prochiral olefins, especially vinylaromatic monomers. The resulting polymers have a syndiotactic stereostructure. More particularly, the present process allows for the preparation of such polymers in high efficiency and having a desired low molecular weight less than 500,000.

It is previously known in the art to prepare highly syndiotactic vinyl aromatic polymers and other prochiral olefins by the use of titanium complexes containing a single cyclopentadienyl or substituted cyclopentadienyl group and an activating cocatalyst including alkylalumoxanes, inert, non-coordinating ion forming compounds, Lewis acids and mixtures thereof. Disclosures of such prior art processes are found in U.S. Pat. Nos. 5,045,517, 5,066,741, 5,206,197 and WO 92/05823 (equivalent to U.S. Ser. No. 07/740529, filed Aug. 5, 1991. The teachings of all of the foregoing patents and patent applications and publications is hereby incorporated by reference.

Generally, the preparation of lower molecular weight polymers by means of a Ziegler-Natta metallocene catalyst is more difficult than the preparation of higher molecular weight polymers. Previously utilized polymerization processes have controlled the molecular weight of the resulting polymer by the use of a variety of chain transfer agents which interrupt the polymerization process causing the formation of lower molecular weight polymers. In the preparation of syndiotactic polymers of vinylaromatic monomers, chain transfer agents normally used in aliphatic olefin polymerizations have proven ineffective or inconvenient to use in the desired reaction equipment. In the absence of chain transfer agents, syndiotactic olefin polymers of molecular weight greater than 500,000 and often greater than 600,000 are generally prepared. Such polymers are difficult to process efficiently without undesired decomposition due to high temperatures. Consequently, there exists a need in the art for an efficient, highly productive process to prepare syndiotactic olefin polymers, particularly, syndiotactic vinyl aromatic polymers, having reduced molecular weight.

SUMMARY OF THE INVENTION

According to the present invention there is provided a process for preparing polymers of prochiral olefin monomers having high stereo-regularity and a molecular weight less than 500,000 comprising contacting the monomer with a catalyst comprising:

1) at least one metal-complex corresponding to the formula:

$AMX_pX'_q$ wherein:
M is titanium, zirconium or hafnium in the +2, +3 or +4 formal oxidation state;
A is an octahydrofluorenyl group or an octahydrofluorenyl group substituted with from 1 to 9 hydrocarbyl groups, each such hydrocarbyl group having up to 10 carbon atoms;
X is an anionic ligand group having up to 40 atoms exclusive of the class of ligands that are cyclic, delocalized, n-bound ligand groups;
X' independently each occurrence is a neutral Lewis base ligating compound, having up to 20 atoms;
p is 1, 2 or 3, and is one less than the formal oxidation state of M;
q is 0, 1 or 2; and 2) an activating cocatalyst
the molar ratio of 1) to 2) being from 1:10,000 to 100:1, or the reaction product formed by converting 1) to an active catalyst by use of an activating technique.

The present process results in the highly efficient production of highly syndiotactic polymers over a wide range of polymerization conditions. In particular the process has been found to be suitable for use in the preparation of monovinylidene aromatic polymers that are highly syndiotactic.

DETAILED DESCRIPTION

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

Prochiral olefins as used herein are $C_{3-20}$ aliphatic or aromatic compounds containing vinylic unsaturation and containing an asymmetrically substituted carbon atom capable of producing stereo regular polymers.

As used herein, the term "syndiotactic" refers to polymers having a stereoregular structure of greater than 50 percent, preferably greater than 75 percent syndiotactic of a racemic triad as determined by $^{13}C$ nuclear magnetic resonance spectroscopy. Such polymers may be usefully employed in the preparation of articles and objects via compression molding, injection molding or other suitable technique having an extremely high resistance to deformation due to the effects of temperature.

Preferred X' groups are carbon monoxide; phosphines, especially trimethylphosphine, triethylphosphine, triphenylphosphine and bis(1,2-dimethylphosphino)ethane; $P(OR)_3$, wherein R is as previously defined; ethers, especially tetrahydrofuran; amines, especially pyridine, bipyridine, tetramethylethylenediamine (TMEDA), and triethylamine.

Preferred coordination complexes used according to the present invention are complexes corresponding to the formula:

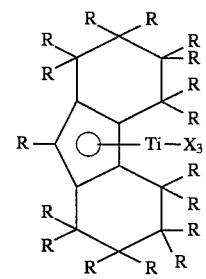

wherein:
R is hydrogen or $C_{1-10}$ alkyl; and
X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy- and di(hydrocarbyl)phosphino-substituted derivatives thereof, said X group having up to 20 nonhydrogen atoms. More preferred X groups are chloride, R', OR', or NR'$_2$, wherein R' is C$_{1-10}$ hydrocarbyl. Especially suited are chloro, methyl, methoxy, phenoxy, isopropoxy, dimethylamido, allyl, methyl-substituted allyl, pentadienyl, 3-methylpentadienyl, and 2,4-dimethylpentadienyl groups.

Most preferred coordination complexes used according to the present invention are complexes corresponding to the formula:

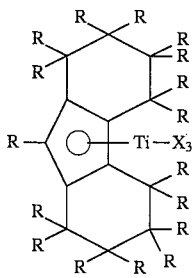

wherein:

R each occurrence is hydrogen; and

X is chloride, C$_{1-4}$ alkoxide or phenoxide.

Examples of the above metal complexes include:

octahydrofluorenyltitanium (IV) trichloride; octahydrofluorenyltitanium (IV) trimethoxide; octahydrofluorenyltitanium (IV) triphenoxide; octahydrofluorenyltitanium (IV) dichloride phenoxide; octahydrofluorenyltitanium (III) dimethoxide; octahydrofluorenyltitanium (III) methyl (2-dimethylaminobenzyl); octahydrofluorenyltitanium (II) allyl (s-cis 1,4-diphenylbutadiene); and octahydrofluorenyltitanium (II) 2,4-dimethylpentadienyl. Additional complexes that are variously substituted as herein defined will be readily apparent to the skilled artisan.

Highly preferred metal complexes are octahydrofluorenyltitanium (IV) trichloride, and octahydrofluorenyltitanium (IV) trimethoxide.

In general, the complexes can be prepared by combining octahydrofluorenyltrimethylsilane (or a ring substituted derivative thereof) with a compound of the formula MX$_{p+1}$X'$_q$. Alternative X ligands may be substituted by use of a Grignard reaction. Optionally a reducing agent can be employed to produce the lower oxidation state complexes. The reactions are conducted in a suitable noninterfering solvent at a temperature from −100° to 300 ° C., preferably from −78° to 100 ° C., most preferably from 0 to 50 ° C. By the term "reducing agent" herein is meant a metal or compound which, under reducing conditions causes the metal M, to be reduced from a higher to a lower oxidation state. Examples of suitable metal reducing agents are alkali metals, alkaline earth metals, aluminum and zinc, alloys of alkali metals or alkaline earth metals such as sodium/mercury amalgam and sodium/potassium alloy. Examples of suitable reducing agent compounds are sodium naphthalenide, potassium graphite, lithium alkyls, lithium or potassium alkadienyls; and Grignard reagents. Most preferred reducing agents are the alkali metals or alkaline earth metals, especially lithium and magnesium metal.

Suitable reaction media for the formation of the complexes include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, and xylene, C$_{1-4}$ dialkyl ethers, C$_{1-4}$ dialkyl ether derivatives of (poly)alkylene glycols, and tetrahydrofuran. Mixtures of the foregoing are also suitable.

The complexes are rendered catalytically active by combination with an activating cocatalyst or by use of an activating technique. Suitable activating cocatalysts for use herein include polymeric or oligomeric alumoxanes, especially methylalumoxane, triisobutyl aluminum modified methylalumoxane, or isobutylalumoxane; neutral Lewis acids, such as C$_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluorophenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium- salts of compatible, noncoordinating anions, or ferrocenium salts of compatible, noncoordinating anions; bulk electrolysis (explained in more detail hereinafter); and combinations of the foregoing activating cocatalysts and techniques. The foregoing activating cocatalysts and activating techniques have been previously taught with respect to different metal complexes in the following references: EP-A-277,003, U.S. Pat. No. 5,153,157, U.S. Pat. No. 5,064,802, EP-A-468,651 (equivalent to U.S. Ser. No. 07/547,718 now abandoned), EP-A-520,732 (equivalent to U.S. Ser. No. 07/876,268), and WO/U.S. Pat. No. 93/23412 (equivalent to U.S. Ser. No. 07/884,966 filed May 1, 1992), now U.S. Pat. No. 5,350,723 the teachings of which are hereby incorporated by reference.

Combinations of neutral Lewis acids, especially the combination of a trialkyl aluminum compound having from 1 to 4 carbons in each alkyl group and a halogenated tri(hydrocarbyl)boron compound having from 1 to 20 carbons in each hydrocarbyl group, especially tris(pentafluorophenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts.

Suitable ion forming compounds useful as cocatalysts in one embodiment of the present invention comprise a cation which is a Bronsted acid capable of donating a proton, and a compatible, noncoordinating anion, A−. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

$$(L^*-H)_d^+(A^{d-})$$

wherein:

L* is a neutral Lewis base;

$(L^*-H)^+$ is a Bronsted acid;

$A^{d-}$ is a noncoordinating, compatible anion having a charge of d−, and d is an integer from 1 to 3.

More preferably $A^{d-}$ corresponds to the formula: $[M'_k{}^+ Q_{n'}]^{d-}$ wherein:

k is an integer from 1 to 3;

n' is an integer from 2 to 6;

n'−k=d;

M' is an element selected from Group 13 of the Periodic Table of the Elements; and Q independently each occurrence is selected from hydride, dialkylamido, halide, hydrocarbyl, hydrocarbyloxide, halosubstituted-hydrocarbyl, halosubstituted hydrocarbyloxy, and halo- substituted silylhydrocarbyl radicals (including perhalogenated hydrocarbyl- perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433, the teachings of which are herein incorporated by reference.

In a more preferred embodiment, d is one, that is, the counter ion has a single negative charge and is A−. Activating cocatalysts comprising boron which are particularly useful in the preparation of catalysts of this invention may be represented by the following general formula: $(L^*-H)^+(BQ_4)^-$;

wherein:

L* is as previously defined;

B is boron in a oxidation state of 3; and

Q is a hydrocarbyl-, hydrocarbyloxy-, fluorinated hydrocarbyl-, fluorinated hydrocarbyloxy-, or fluorinated silylhydrocarbyl- group of up to 20 nonhydrogen atoms, with the proviso that in not more than one occasion is Q hydrocarbyl.

Most preferably, Q is each occurrence a fluorinated aryl group, especially, a pentafluorophenyl group.

Illustrative, but not limiting, examples of boron compounds which may be used as an activating cocatalyst in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-2,4,6-trimethylanilinium tetraphenylborate, trimethylammonium tetrakis(pentafluorophenyl) borate, triethylammonium tetrakis(pentafluorophenyl) borate, tripropylammonium tetrakis(pentafluorophenyl) borate, tri(n-butyl)ammonium tetrakis(pentafluorophenyl) borate, tri(sec-butyl)ammonium tetrakis(pentafluorophenyl) borate, N,N-dimethylanilinium tetrakis(pentafluorophenyl) borate, N,N-dimethylanilinium n-butyltris(pentafluorophenyl) borate, N,N-dimethylanilinium benzyltris(pentafluorophenyl) borate, N,N-dimethylanilinium tetrakis(4-(t-butyldimethylsilyl)- 2, 3, 5, 6-tetrafluorophenyl) borate, N,N-dimethylanilinium tetrakis(4-(triisopropylsilyl)-2, 3, 5, 6-tetrafluorophenyl) borate, N,N-dimethylanilinium pentafluorophenoxy-tris(pentafluorophenyl) borate, N,N-diethylanilinium tetrakis(pentafluorophenyl) borate, N,N-dimethyl-2,4,6-trimethylanilinium tetrakis-(pentafluorophenyl) borate, trimethylammonium tetrakis(2,3,4,6-tetrafluorophenyl) borate triethylammonium tetrakis(2,3,4,6-tetrafluorophenyl) borate, tripropylammonium tetrakis(2,3,4,6-tetrafluorophenyl) borate, tri(n-butyl)ammonium tetrakis(2,3,4,6-tetrafluorophenyl) borate, dimethyl(t-butyl)ammonium tetrakis(2,3,4,6-tetrafluorophenyl) borate, N,N-dimethylanilinium tetrakis(2,3,4,6-tetrafluorophenyl) borate, N,N-diethylanilinium tetrakis(2,3,4,6-tetrafluorophenyl) borate, and N,N-dimethyl-2,4,6-trimethylanilinium tetrakis(2,3,4,6-tetrafluorophenyl) borate;

dialkyl ammonium salts such as:

di-(i-propyl)ammonium tetrakis(pentafluorophenyl) borate, and dicyclohexylammonium tetrakis(pentafluorophenyl) borate;

tri-substituted phosphonium salts such as:

triphenylphosphonium tetrakis(pentafluorophenyl) borate, tri(o-tolyl)phosphonium tetrakis(pentafluorophenyl) borate, and tri(2,6-dimethylphenyl)phosphonium tetrakis(pentafluorophenyl) borate;

di-substituted oxonium salts such as:

diphenyloxonium tetrakis(pentafluorophenyl) borate, di(o-tolyl)oxonium tetrakis(pentafluorophenyl) borate, and di(2,6-dimethylphenyl)oxonium tetrakis(pentafluorophenyl) borate;

di-substituted sulfonium salts such as:

diphenylsulfonium tetrakis(pentafluorophenyl) borate, di(o-tolyl)sulfonium tetrakis(pentafluorophenyl) borate, and bis(2,6-dimethylphenyl)sulfonium tetrakis(pentafluorophenyl) borate.
and tributylammonium.

Another suitable ion forming, activating cocatalyst comprises a salt of a cationic oxidizing agent and a noncoordinating, compatible anion represented by the formula: $(Ox^{e+})_d(A^{d-})_e$.

wherein:

$Ox^{e+}$ is a cationic oxidizing agent having a e is an integer from 1 to 3; and $A^{d-}$ and d are as previously defined.

Examples of cationic oxidizing agents include: ferrocenium, hydrocarbyl-substituted ferrocenium, $Ag^+$, or $Pb^{+2}$.

Preferred embodiments of $A^{d-}$ are those anions previously defined with respect to the Bronsted acid containing activating cocatalysts, especially tetrakis(pentafluorophenyl)borate.

Another suitable ion forming, activating cocatalyst comprises a compound which is a salt of a carbenium ion and a noncoordinating, compatible anion represented by the formula: $\copyright^+ A^-$
wherein:

$\copyright^+$ is a $C_{1-20}$ carbenium ion; and $A^-$ is as previously defined. A preferred carbenium ion is the trityl cation, i.e. triphenylmethylium.

A further suitable ion forming, activating cocatalyst comprises a compound which is a salt of a silylium ion and a noncoordinating, compatible anion represented by the formula: $R_3Si(X')_q^+A^-$
wherein:

R is $C_{1-10}$ hydrocarbyl, and X', q and $A^-$ are as previously defined.

Preferred silylium salt activating cocatalysts are trimethylsilylium tetrakispentafluorophenylborate, triethylsilylium tetrakispentafluorophenylborate and ether substituted adducts thereof. Silylium salts have been previously generically disclosed in *J. Chem Soc. Chem. Comm.*, 1993, 383–384, as well as Lambert, J. B., et al., *Organometallics*, 1994, 13, 2430–2443. The use of the above silylium salts as activating cocatalysts for addition polymerization catalysts is claimed in United States Patent Application entitled, Silylium Cationic Polymerization Activators For Metallocene Complexes, filed in the names of David Neithamer, David Devore, Robert LaPointe and Robert Mussell on Sep. 12, 1994.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433, the teachings of which are herein incorporated by reference. Preferred complexes include phenol, especially fluorinated phenol adducts of tris(pentafluorophenyl)borane. The latter cocatalysts are disclosed and claimed in United States Patent Application entitled, Phenol-Borane Adduct Polymerization Activators For Metallocene Complexes, filed in the name of Peter Nickias on Sep. 12, 1994.

The technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are: liquids under the conditions of the electrolysis (generally temperatures from 0° to 100 ° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), dimethoxyethane (DME), and mixtures thereof.

The electrolysis may be conducted in a standard electrolytic cell containing an anode and cathode (also referred to as the working electrode and counter electrode respectively). Suitable materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and a compatible, noncoordinating anion, $A^-$. Preferred supporting electrolytes are salts corresponding to the formula $G^+A^-$; wherein:

$G^+$ is a cation which is nonreactive towards the starting and resulting complex, and $A^-$ is as previously defined.

Examples of cationst $G^+$, include tetrahydrocarbyl substituted ammonium or phosphonium cations having up to 40 nonhydrogen atoms. Preferred cations are the tetra(n-butylammonium)- and tetraethylammonium- cations.

During activation of the complexes of the present invention by bulk electrolysis the cation of the supporting electrolyte passes to the counter electrode and A- migrates to the working electrode to become the anion of the resulting oxidized product. Either the solvent or the cation of the supporting electrolyte is reduced at the counter electrode in equal molar quantity with the amount of oxidized metal complex formed at the working electrode. Preferred supporting electrolytes are tetrahydrocarbylammonium salts of tetrakis(perfluoroaryl) borates having from 1 to 10 carbons in each hydrocarbyl or perfluoroaryl group, especially tetra(n-butylammonium)tetrakis(pentafluorophenyl) borate.

A further recently discovered electrochemical technique for generation of activating cocatalysts is the electrolysis of a disilane compound in the presence of a source of a noncoordinating compatible anion. This technique is more fully disclosed and claimed in the previously mentioned U.S. patent application entitled, "Silylium Cationic Polymerization Activators For Metallocene Complexes", filed on Sep. 12, 1994.

The foregoing activating techniques and ion forming cocatalysts are also preferably used in combination with a tri(hydrocarbyl)aluminum or tri(hydrocarbyl)borane compound having from 1 to 4 carbons in each hydrocarbyl group, an oligomeric or polymeric alumoxane compound, or a mixture of a tri(hydrocarbyl)aluminum compound having from 1 to 4 carbons in each hydrocarbyl group and a polymeric or oligomeric alumoxane.

The molar ratio of catalyst/cocatalyst employed preferably ranges from 1:10,000 to 100:1, more preferably from 1:5000 to 10:1, most preferably from 1:1000 to 1:1. In a particularly preferred embodiment of the invention the cocatalyst can be used in combination with a tri(hydrocarbyl)aluminum compound having from 1 to 10 carbons in each hydrocarbyl group. Mixtures of activating cocatalysts may also be employed. It is possible to employ these aluminum compounds for their beneficial ability to scavenge impurities such as oxygen, water, and aldehydes from the polymerization mixture. Preferred aluminum compounds include trialkyl aluminum compounds having from 2 to 6 carbons in each alkyl group, especially those wherein the alkyl groups are methyl, ethyl, propyl, isopropyl, n-butyl, isobutyl, pentyl, neopentyl, or isopentyl. Preferred alumoxane compounds are methylalumoxane, modified methylalumoxane (that is, methylalumoxane modified by reaction with triisobutyl aluminum) (MMAO) and isobutylalumoxane. The molar ratio of metal complex to aluminum compound is preferably from 1:10,000 to 100:1, more preferably from 1:1000 to 10:1, most preferably from 1:500 to 1:1.

The most highly preferred activating cocatalyst comprises a mixture of an alkylalumoxane, especially methylalumoxane, isopropylalumoxane or isopropylaluminum modified methylalumoxane in combination with an aluminum trialkyl compound having from 1 to 4 carbons in each alkyl group, especially, triisobutyl aluminum. Preferred ratios of trialkylalumimum compound to alkylalumoxane are from 0.1:1 to 10:1, more preferably from 0.25:1 to 1:1.

The processs may be used to polymerize ethylenically unsaturated monomers having from 3 to 20 carbon atoms either alone or in combination. Preferred monomers include monovinylidene aromatic monomers, 4-vinylcyclohexene, vinylcyclohexane, and $C_{3-10}$ aliphatic α-olefins (especially propylene, isobutylene, 1-butene, 1-hexene, 3-methyl-1-pentene, 4-methyl-1-pentene, and 1-octene), and mixtures thereof. Most preferred monomers are styrene, and $C_{1-4}$ alkyl substituted styrene.

In general, the polymerization may be accomplished at conditions well known in the prior art for Ziegler-Natta or Kaminsky-Sinn type polymerization reactions, i.e., temperatures from 0°–250 ° C., preferably 30° to 85 ° C. and pressures from atmospheric to 10,000 atmospheres. Suspension, solution, slurry, gas phase, solid state powder polymerization or other process condition may be employed if desired. A support, especially silica, alumina, or a polymer (especially poly(tetrafluoroethylene) or a polyolefin) may be employed, and desirably is employed when the catalysts are used in a gas phase polymerization process. The support is preferably employed in an amount to provide a weight ratio of catalyst (based on metal):support from 1:100,000 to 1:10, more preferably from 1:50,000 to 1:20, and most preferably from 1:10,000 to 1:30.

In most polymerization reactions the molar ratio of catalyst:polymerizable compounds employed is from $10^{-12}$:1 to $10^{-1}$:1, more preferably from $10^{-9}$:1 to $10^{-5}$:1.

Suitable solvents for polymerization are inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and the like and aromatic and alkyl-substituted aromatic compounds such as benzene, toluene, xylene, ethylbenzene and the like. Suitable solvents also include liquid olefins which may act as monomers or comonomers including ethylene, propylene, butadiene, cyclopentene, 1-hexene, 1-hexane, 4-vinylcyclohexane, vinylcyclohexane, 3-methyl-1-pentene, 4-methyl-1-pentene, 1,4-hexadiene, 1-octene, 1-decene, styrene, divinylbenzene, allylbenzene, vinyltoluene (including all isomers alone or in admixture), and the like. Mixtures of the foregoing are also suitable.

The catalysts may also be utilized in combination with at least one additional homogeneous or heterogeneous polymerization catalyst in separate reactors connected in series or in parallel to prepare polymer blends having desirable properties. An example of such a process is disclosed in WO 94/00500, equivalent to U.S. Ser. No. 07/904,770, now abandoned as well as U.S. Ser. No. 08/10958, filed Jan. 29, 1993, now abandoned the teachings or which are hereby incorporated by reference herein.

Desirably the polymerization is conducted by contacting the monomer and catalyst composition under conditions to produce a polymer having molecular weight from 200,000 to 450,000. In the determination of such molecular weights herein the technique used is that of solution viscometry using 1,3,5-trichlorobenzene at 135 ° C., calibrated with gel permeation chromatography using an atactic polystyrene standard. The number is a unitless value reflecting the weight average molecular weight, Mw. Efficiencies of the present process are generally sufficient to provide a percent conversion after one hour polymerization of at least 30 weight percent, preferably at least 50 weight percent, most preferably at least 60 weight percent.

The skilled artisan will appreciate that the invention disclosed herein may be practiced in the absence of any component which has not been specifically disclosed. The following examples are provided as further illustration thereof and are not to be construed as limiting. Unless stated to the contrary all parts and percentages are expressed on a weight basis.

EXAMPLE 1

Octahydrofluorenyltitanium trichloride

Octahydrofluorenyltrimethylsilane (prepared by combination of silyl chloride and lithium octahydrofluorenide in tetrahydrofuran (THF)) (0.74 g, 3.0 mmol, in 10 mL THF) was added dropwise to 20 mL of toluene containing 0.57 g (3.0 mmol) of titanium tetrachloride at about 25° C. The solution was stirred for 1 hour. After this time the solvent was removed under reduced pressure. 10 mL of hexane was added to the residue and the solution was cooled to −20° C. for 3 hours. A dark red precipitate was obtained. Washing the solid with hexane left a blue powder which was removed by filtration. The liquid was concentrated and upon cooling gave a red-orange powder which was identified by $^1$H NMR spectroscopy as octahydrofluorenyltitanium trichloride. Yield was 0.263 g, 27 percent.

Polymerization

Small glass ampoules were filled with styrene monomer, methylalumoxane, triisobutyl aluminum and metal complex (octahydrofluorenyltitanium trichloride (OTT) or a comparison metal complex) in quantitites to give a molar ratio of 233,000:200:100:1. The ampoules were sealed and placed in water baths heated to 50° C. and 70° C. respectively. The ampoules were removed after 1 hour and percent conversion and molecular weights determined. Percent conversion was determined by weight loss after devolatilization. Polymer molecular weights were determined by solution viscometry. Comparative metal complexes were pentamethylcyclopentadienyl titanium trichloride (PTT), (1,3-dimethyltetrahydroindenyl) titanium trichloride (ITT) and tetramethylcyclopentadienyl titanium trimethoxide (TTT). Results are contained in Table I.

TABLE I

| Complex | 50° C. Conversion (percent) | 50° C. Mw | 70° C. Conversion (percent) | 70° C. Mw |
|---|---|---|---|---|
| OTT | 64.5 | 410,000 | 53.9 | 260,000 |
| PTT | 61 | 805,000 | 59 | 650,000 |
| ITT | 46.3 | 445,000 | 33 | 230,000 |
| TTT | 59 | 500,000 | 48 | 350,000 |

By reference to the results of Table I, it may be seen that the use of octahydrofluorenyltitanium trichloride metal complex resulted in high efficiency (50° C. and 70° C. conversions after 1 hour greater than 50 percent) while maintaining the polymer molecular weight less than 500,000, preferably less than 450,000.

What is claimed is:

1. A process for preparing polymers of prochiral olefin monomers having high stereo-regularity and a molecular weight less than 500,000 comprising contacting the monomer with a catalyst comprising:

1) at least one metal complex corresponding to the formula:

$AMX_pX'_q$ wherein:
   M is titanium, zirconium or hafnium in the +2, +3 or +4 formal oxidation state;
   A is an octahydrofluorenyl group or an octahydrofluorenyl group substituted with from 1 to 9 hydrocarbyl groups, each such hydrocarbyl group having up to 10 carbon atoms;
   X is an anionic ligand group having up to 40 atoms exclusive of the class of ligands that are cyclic, delocalized, n-bound ligand groups;
   X' independently each occurrence is a neutral Lewis base ligating compound, having up to 20 atoms;
   p is 1, 2 or 3, and is one less than the formal oxidation state of M;
   q is 0, 1 or 2; and 2) an activating cocatalyst
   the molar ratio of 1) to 2) being from 1:10,000 to 100:1, or
   the reaction product formed by converting 1) to an active catalyst by use of an activating technique.

2. A process according to claim 1 wherein the metal complex corresponds to the formula:

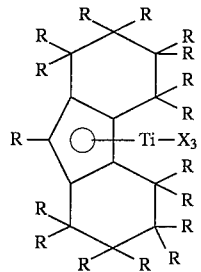

wherein:
R is hydrogen or $C_{1-10}$ alkyl; and
X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy- and di(hydrocarbyl)phosphino-substituted derivatives thereof, said X group having up to 20 nonhydrogen atoms.

3. A process according to claim 1 wherein the metal complex corresponds to the formula:

wherein:
R each occurrence is hydrogen; and
X is chloride, $C_{1-4}$ alkoxide or phenoxide.

4. A process according to claim 1 wherein the metal complex is octahydrofluorenyltitanium trichloride or octahydrofluorenyltitanium trimethoxide.

5. A process according to claim 1 wherein the monomer is selected from the group consisting of $C_{3-10}$ aliphatic α-olefins; monovinylidene aromatic monomers; 4-vinylcyclohexene, vinylcyclohexane; and mixtures thereof.

6. A process according to claim 5 wherein the monomer is a monovinylidene aromatic monomer and the polymer has a syndiotacticity of at least 50 percent at a racemic triad.

7. A process according to claim 6 wherein the catalyst is supported.

8. A process according to claim 1 wherein the molar ratio of catalyst:monomer is from $10^{-12}:1$ to $10^{-1}:1$.

* * * * *